United States Patent
Liporace et al.

(10) Patent No.: US 9,333,526 B2
(45) Date of Patent: May 10, 2016

(54) DEVICE FOR COATING BONE PLATE

(76) Inventors: Frank A. Liporace, Englewood Cliffs, NJ (US); Richard S. Yoon, New York, NY (US)

(*) Notice: Subject to any disclaimer, the term of this patent is extended or adjusted under 35 U.S.C. 154(b) by 169 days.

(21) Appl. No.: 13/985,329

(22) PCT Filed: Feb. 17, 2012

(86) PCT No.: PCT/US2012/025682
§ 371 (c)(1),
(2), (4) Date: Aug. 14, 2013

(87) PCT Pub. No.: WO2012/112915
PCT Pub. Date: Aug. 23, 2012

(65) Prior Publication Data
US 2013/0319322 A1     Dec. 5, 2013

Related U.S. Application Data

(60) Provisional application No. 61/443,953, filed on Feb. 17, 2011.

(51) Int. Cl.
| | |
|---|---|
| *B05C 13/02* | (2006.01) |
| *A61B 17/80* | (2006.01) |
| *A61B 17/00* | (2006.01) |
| *A61F 2/30* | (2006.01) |
| *A61B 17/82* | (2006.01) |

(52) U.S. Cl.
CPC ............... *B05C 13/02* (2013.01); *A61B 17/80* (2013.01); *A61B 17/82* (2013.01); *A61B 2017/00004* (2013.01); *A61B 2017/00526* (2013.01); *A61F 2002/30677* (2013.01); *A61F 2310/0097* (2013.01)

(58) Field of Classification Search
None
See application file for complete search history.

(56) References Cited

U.S. PATENT DOCUMENTS

| | | |
|---|---|---|
| 4,513,744 A | 4/1985 | Klaue |
| 4,957,497 A | 9/1990 | Hoogland et al. |
| 5,129,899 A | 7/1992 | Small et al. |
| 5,735,853 A | 4/1998 | Olerud |
| 5,741,258 A | 4/1998 | Klaue et al. |

(Continued)

OTHER PUBLICATIONS

Bozic, Kevin J., "The Impact of Infection After Total Hip Arthroplasty on Hospital and Surgeon Resource Utilization", J. Bone Joint Surg. 87A, 8, pp. 1746-1751 (Aug. 2005).

(Continued)

*Primary Examiner* — Dah-Wei D Yuan
*Assistant Examiner* — Jethro M Pence
(74) *Attorney, Agent, or Firm* — Cowan, Liebowitz & Latman, P.C.; Brian R. Volk

(57) ABSTRACT

An encasement for coating a bone plate with a substrate includes a sidewall structure having an upper edge and a cover disposed on the upper edge of the sidewall structure. The encasement includes a base from which the sidewall structure rises such that the sidewall structure, the cover and the base combine to create an open interior space of the encasement. An aperture in the sidewall structure provides access to the open interior space of the encasement and a plurality of cover protrusions extend from the cover into the open interior space. The encasement further includes a plurality of base protrusions extending from the base directly opposing the plurality of cover protrusions. A combined height of an individual cover protrusion and an opposing base protrusion is less than or equal to a height of the sidewall structure.

12 Claims, 5 Drawing Sheets

(56) References Cited

U.S. PATENT DOCUMENTS

| | | | |
|---|---|---|---|
| 5,931,838 A | 8/1999 | Vito | |
| 6,315,779 B1 | 11/2001 | Morrison et al. | |
| 6,503,250 B2 | 1/2003 | Paul | |
| 6,695,846 B2 | 2/2004 | Richelsoph et al. | |
| 6,719,759 B2 | 4/2004 | Wagner et al. | |
| 2003/0159806 A1* | 8/2003 | Sehmbey et al. | 165/80.3 |
| 2004/0092939 A1 | 5/2004 | Freid et al. | |
| 2004/0102776 A1 | 5/2004 | Huebner | |
| 2005/0049593 A1 | 3/2005 | Duong et al. | |
| 2006/0198110 A1 | 9/2006 | Hunkeler et al. | |
| 2006/0228464 A1 | 10/2006 | Larson et al. | |
| 2009/0217872 A1 | 9/2009 | Sauer et al. | |
| 2011/0011339 A1 | 1/2011 | Pei | |
| 2011/0054476 A1* | 3/2011 | Nardini | A61B 17/8033 606/70 |

OTHER PUBLICATIONS

Brinker, Mark R., "The Incidence of Fractures and Dislocations Referred for Orthopaedic Services in a Capitated . . . ", J. Bone Joint Surg. 86A, 2, pp. 290-297, (Feb. 2004).

Davidson, Darren, "Intraoperative Periprosthetic Fractures During Total Hip Arthroplasty", J. Bone Joint Surg. Am. 90A, 9, pp. 2000-2012 (Sep. 2008).

Del Pozo, Jose L., "Infection Associated with Prosthetic Joints", N. Engl. J. Med. 361, 8, pp. 787-794 (Aug. 2009).

Karunakar, Madhav A., "Does Stress-Induced Hyperglycemia Increase the Risk of Perioperative Infectious . . . " J. Orthop. Trauma 24, 12, pp. 752-756 (Dec. 2010).

International Search Report and Written Opinion of the International Searching Authority, 9 pages (Jul. 2012).

* cited by examiner

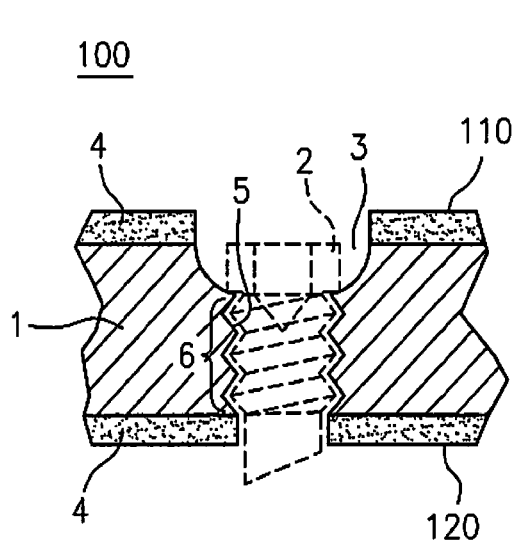
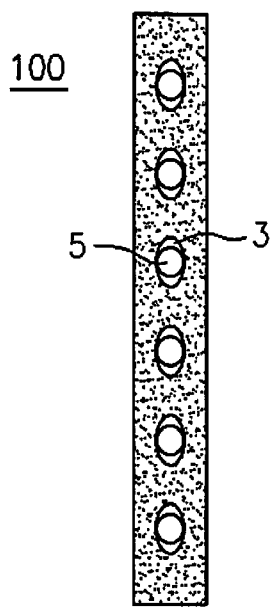
FIG. 1
FIG. 2
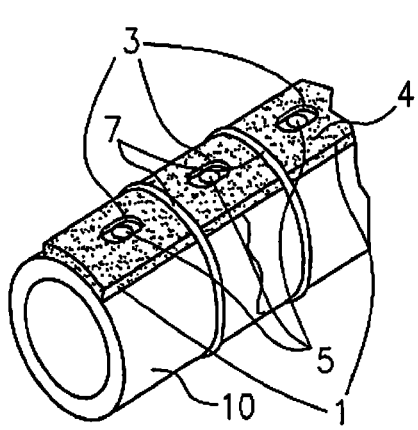
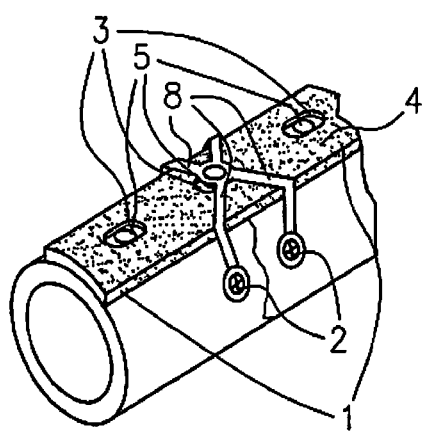
FIG. 3
FIG. 4

DEVICE FOR COATING BONE PLATE

PRIORITY

This application claims priority to U.S. Provisional Application No. 61/443,953, filed Feb. 17, 2011, the entire contents of which are incorporated herein by reference.

BACKGROUND OF THE INVENTION

1. Field of the Invention

The present invention relates generally to surgical devices, and more particularly, to a device for coating bone plates with a medical coating.

2. Brief Description of the Related Art

In the United States, bone fracture and musculoskeletal infection result in over 1 million hospital visits per year, amounting to billions of dollars in direct health care and hospital costs. The rising elderly, diabetic and obese populations present an increased risk of fracture and infection resulting in a higher number of patients receiving total joint replacements who are at subsequent risk for periprosthetic fracture, i.e., fractures around joint replacement prostheses.

Fracture stabilization with proper component alignment and maintenance, along with prevention of fracture propagation via Open Reduction Internal Fixation (ORIF), have been favorable in treating periprosethetic fracture. However, periprosthetic fractures come with an increased risk of periprosthetic infection, and there is a need to minimize costs via reduction of re-operations and associated complications. Infection and fracture around a prosthetic joint leads to decreased clinical function and patient satisfaction and often requires several reoperations and long-term antibiotic regimens.

Infection following Total Hip Arthroplasty (THA), for example, is a complication with limited treatment options. Treatment protocols range from articulating component exchange with debridement, one-stage revision, and two-stage revision. Timing of infection, whether acute or chronic, helps selection of treatment protocol. Individually encountered, favorable management of either periprosthetic fracture or infection is achievable. However, when faced with fracture and an associated infection, little guidance is available for proper management.

SUMMARY OF THE INVENTION

According to an embodiment of the present invention, an encasement is provided for coating a bone plate with a substrate. The encasement includes a sidewall structure having an upper edge and a cover disposed on the upper edge of the sidewall structure. The encasement further includes a base from which the sidewall structure rises such that the sidewall structure, the cover and the base combine to create an open interior space of the encasement. An aperture in the sidewall structure provides access to the open interior space of the encasement and a plurality of cover protrusions extend from the cover into the open interior space. The encasement further includes a plurality of base protrusions extending from the base directly opposing the plurality of cover protrusions. A combined height of an individual cover protrusion and an opposing base protrusion is less than or equal to a height of the sidewall structure.

According to an embodiment of the present invention, an encasement is provided for coating a bone plate with a substrate. The encasement includes a sidewall structure having an upper edge, a cover disposed on the upper edge of the sidewall structure, and a base from which the sidewall structure rises. The sidewall structure, the cover and the base combine to create an open interior space of the encasement. The encasement further includes an aperture in the sidewall structure providing access to the open interior space of the encasement, and a plurality of interior walls disposed in the open interior space. Each of the plurality of interior walls comprises a segment with a height that is less than a height of the sidewall structure.

According to an embodiment of the present invention, an encasement is provided for coating a bone plate with a substrate. The encasement includes a sidewall structure having an upper edge and a cover disposed on the upper edge of the sidewall structure. The sidewall structure and the cover combine to create an open interior space of the encasement. The encasement further includes an aperture in the sidewall structure providing access to the open interior space of the encasement and a plurality of cover protrusions extending from the cover. A combined height of an individual cover protrusion and an opposing base protrusion is less than or equal to a height of the sidewall structure.

BRIEF DESCRIPTION OF THE DRAWINGS

The above and other objects, features and advantages of certain embodiments of the present invention will be more apparent from the following detailed description taken in conjunction with the accompanying drawings, in which:

FIG. 1 is a diagram illustrating a cross-sectional view of an implant article according to an embodiment of the present invention;

FIG. 2 is a diagram illustrating a bone plate coated with a substrate, according to an embodiment of the present invention;

FIG. 3 is a diagram illustrating a bone plate affixed to a bone, according to an embodiment of the present invention;

FIG. 4 is a diagram illustrating a bone plate and locking elements, according to an embodiment of the present invention;

DETAILED DESCRIPTION OF EMBODIMENTS OF THE PRESENT INVENTION

Figure 5:
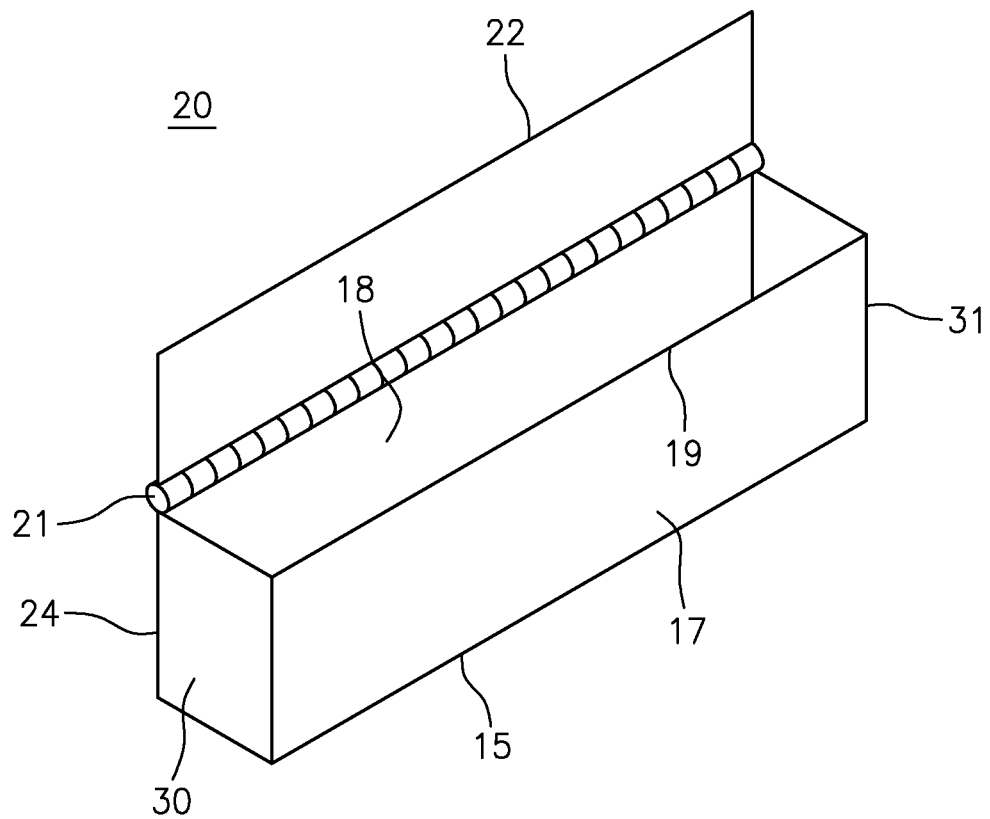
FIG. 5 is a diagram illustrating an encasement, according to an embodiment of the present invention.

The following detailed description of embodiments of the invention will be made in reference to the accompanying drawings. In describing the invention, explanation about related functions or constructions known in the art are omitted for the sake of clearness in understanding the concept of the invention to avoid obscuring the invention with unnecessary detail.

A device is provided for coating a bone plate with a medical coating. The coated bone plate stabilizes a periprosthetic fracture and reduces prosthetic infection. The device is especially useful in a fracture pattern with extensive propagation warranting stabilization. According to an embodiment of the present invention, a mold is provided for coating the bone plate with the medical coating. The medical coating includes bone cement impregnated with antibiotics and/or growth factors for treatment or prevention of periprosthetic infection.

Local delivery of antibiotics and/or other growth factors via a cement-loaded and coated bone plate provides antibacterial properties. Embodiments of the present invention enable consistent and efficient medical coating of bone plates, which vary in size and shape based on the bones to which they are applied.

Utilizing the device reduces risk of additional operations by providing bone stability and anti-infective properties. The device may be utilized for bone plates configured for fractures anywhere in the body that have a risk for infection or have an active infection, with or without surrounding prosthetics.

Referring initially to FIG. 1, FIG. 1 illustrates a cross-sectional view of an implant article according to an embodiment of the present invention. Specifically, FIG. 1 illustrates a bone plate 100 including a plate body 1. The plate body 1 is preferably coated with a medical coating including a resorbable or non-resorbable substrate 4 for delivering medication including, for example, bone cement impregnated with antibiotics and/or growth factors. The bone plate 100 is an implant utilized for bone fixation. A number of bone screw holes 5 extending through the plate body 1 are provided for bone screws 2, which are inserted in an interlocking, or threaded, fashion. The bone screw hole 5 is threaded according to methods specific to the medical field. In accordance with another embodiment of the present invention the bone screws 2 can be provided in a non-interlocking, or non-threaded, fashion. Locking elements 6 define the bone screw hole 5 disposed in a recessed manner in an elongated opening 3. The locking elements 6 are preferably not coated by the substrate 4 in order to allow for proper attachment with the bone screws 2.

The elongated opening 3 is inset from a top surface 110 of the plate body 1. The elongated opening 3 is embodied as a groove that is deeper than a top of a bone screw 2 when the bone screw 2 is inserted into the bone screw hole 5. The elongated opening 3 allows for variable angled insertion of bone screws 2 in order to achieve maximum fixation across the fracture site. The bone screw hole 5 and the bone screws 2 are designed specifically for the medical field to allow the variable angled insertion. The elongated opening 3 provides an angular range of freedom up to about 15 degrees in any direction. The elongated opening 3 is illustrated as being on the top surface 110, in FIG. 1, however alternate embodiments of the present invention also include the elongated opening 3 on a bottom surface 120 of the bone plate 100 to allow for insertion of the bone screws 2 through the bone screw holes 5 at varying angles.

The bone plate 100 is coated with the substrate 4, which includes antibiotic coatings, growth factor coatings, bone cement, and bone cement impregnated with, for example, antibiotics and/or growth factors. The substrate 4 may be applied in a 1:10 gram (g) ratio of antibiotic to bone cement, though other ratios may range from 0.5:10 g to 1.5:10 g. Dosing of the substrate can range from 1.0 g, 1.5 g, 2.0 g, 2.5 g, 3.0 g, 3.5 g, and 4.0 g of antibiotic and/or growth factors at respective 10 g ratios of 10 g, 15 g, 20 g, 25 g, 30 g, 35 g or 40 g of bone cement, respectively.

Referring now to FIG. 2, FIG. 2 illustrates a bone plate coated with a substrate, according to an embodiment of the present invention. Specifically, FIG. 2 illustrates the bone plate 100 including the bone screw holes 5 centered in the elongated openings 3. The elongated opening 3 in FIG. 2 is illustrated as an oval-shape, but is not limited thereto and may be embodied as any shape allowing for varying angles of insertion of the bone screws 2 through the bone screw holes 5. Further, while FIG. 2 illustrates a rectangular bone plate with a straight line of openings, the bone plate may be embodied as any type of shape to accommodate the bone having the fracture. Additionally, the openings in the bone plate may be in any pattern that allows for proper securing of the bone plate to the bone based on the bone with the fracture and the shape of the bone plate.

Referring now to FIG. 3, FIG. 3 illustrates a bone plate affixed to a bone, according to an embodiment of the present invention. Specifically, FIG. 3 illustrates the bone plate 100 being secured to a bone 10 via cables 7. The bone screw holes 5 on the plate body 1 include the elongated opening 3. The bone screw holes 5 are preferably not coated with the substrate 4 in order to allow for complete and rigid fixation of the bone screws 2 with the bone 10. The bone plate 100 provides bone fixation and stabilization of an acute fracture, in particular a fracture having an active infection, healing difficulty, or a risk of infection.

Referring now to FIG. 4, FIG. 4 illustrates a bone plate and locking elements, according to an embodiment of the present invention. Specifically, FIG. 4 illustrates the bone plate 100 secured to the bone 10 plating system 8. The plating system 8 allows insertion of screws at various locations on the bone 10. The plating system 8 also is attached to the bone 10 by bone screws 2 applied through the bone screw holes 5. The plating system 8 may be used to secure the bone plate 100 when a rod is necessary to secure the fracture site and is placed through the bone 10. The plating system 8 allows for shallow insertion of the bone screws 2 to avoid contacting the rod within the bone 10. Alternate embodiments for securing the bone plate 100 to the bone 10 may also be utilized, and the present invention is not limited to those described herein.

Referring now to FIG. 5, FIG. 5 illustrates a bone plate encasement, according to an embodiment of the present invention. Specifically, FIG. 5 illustrates a bone plate encasement 20 that encapsulates the bone plate 100 for coating with the substrate 4. The encasement 20 facilitates coating of the bone plate 100 while maintaining patency and integrity of the screw holes for future fastening. Prior to implantation of the bone plate 100, the bone plate 100 is placed within an open interior space of the encasement 20, which provides a mold for coating the bone plate 100 with the substrate 4. Although shown as rectangular in FIG. 5, the encasement 20 may vary in size and shape depending on the size and shape of the bone plate to be coated.

The encasement 20 includes a cover 22, a sidewall structure, and a base 15. The sidewall structure includes a first sidewall 17, a second sidewall 18, a first end 30, and a second end 31. An upper edge 19 of the encasement 20 defines a periphery of an upper surface of the encasement 20 and extends along the first sidewall 17, the second sidewall 18, the first end 30, and the second end 31. The cover 22 is removably attached to and encloses the upper surface of the encasement 20 and is secured to the second sidewall 18 by a hinge 21 that is disposed along the upper edge 19 of the encasement 20. The hinge 21 is disposed on the edge 19 of the encasement 20 where the second sidewall 18 and the cover 22 converge. The first sidewall 17, the second sidewall 18, the first end 30 and the second end 31 extend substantially perpendicularly between the cover 22 and the base 15 when the cover 22 is closed, and surround the bone plate 100 when the bone plate 100 is placed within the encasement 20.

According to an embodiment of the present invention, the first sidewall 17, the second sidewall 18, the first end 30 and the second end 31 may extend between the cover 22 and the base 15 at various angles according to the shape of the bone plate being coated. Further, the attachment of the cover 22 is not limited to the hinge 21 described above. In another embodiment of the present invention, the cover 22 includes a groove the runs around a periphery of the cover 22 for snapping the cover 22 over the edge 19 of the first sidewall 17, the second sidewall 18, the first end 30 and the second end 31.

In another embodiment of the present invention, the cover 22 is divided into sections by a hinge. An axis of the hinge may run parallel with the first and second sidewalls 17 and 18, or the first and second ends 30 and 31. The divided cover 22 allows access to a portion of the interior space of the encasement 20 without opening the entire interior space of the encasement 20. Thus, the hinge 21 not limited to being positioned on the edge 19 of the second sidewall 18 of the encasement 20.

Figure 6:
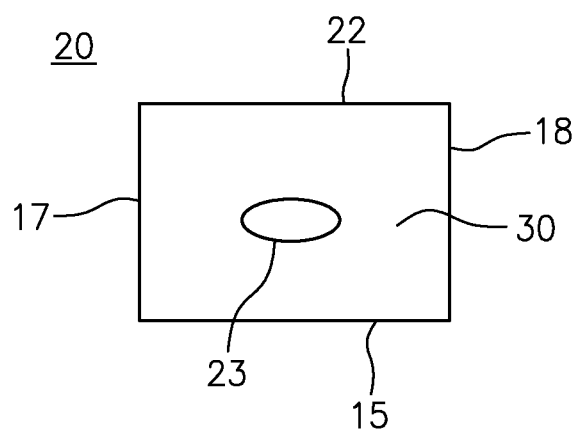
FIG. 6 is a diagram illustrating an end-view of an encasement, which shows a substrate introduction aperture, according to an embodiment of the present invention.

Referring now to FIG. 6, FIG. 6 illustrates an end-view of an encasement, which shows a substrate introduction aperture, according to an embodiment of the present invention. Specifically, FIG. 6 illustrates the first end 30 of the encasement 20 having a substrate introduction aperture 23, which acts as a conduit for a substrate applicator, e.g., a bone cement gun, to inject the substrate 4. Excess substrate 4 observed through the substrate aperture 23 may be used as an indirect timer to identify hardening of the substrate 4. Upon hardening, the encasement 20 is opened at the cover 22, via the hinge 21 and the completely coated bone plate 100 is removed. The substrate aperture 23 may vary in size and shape based on the substrate applicator being used to inject the substrate 4.

Figure 7:
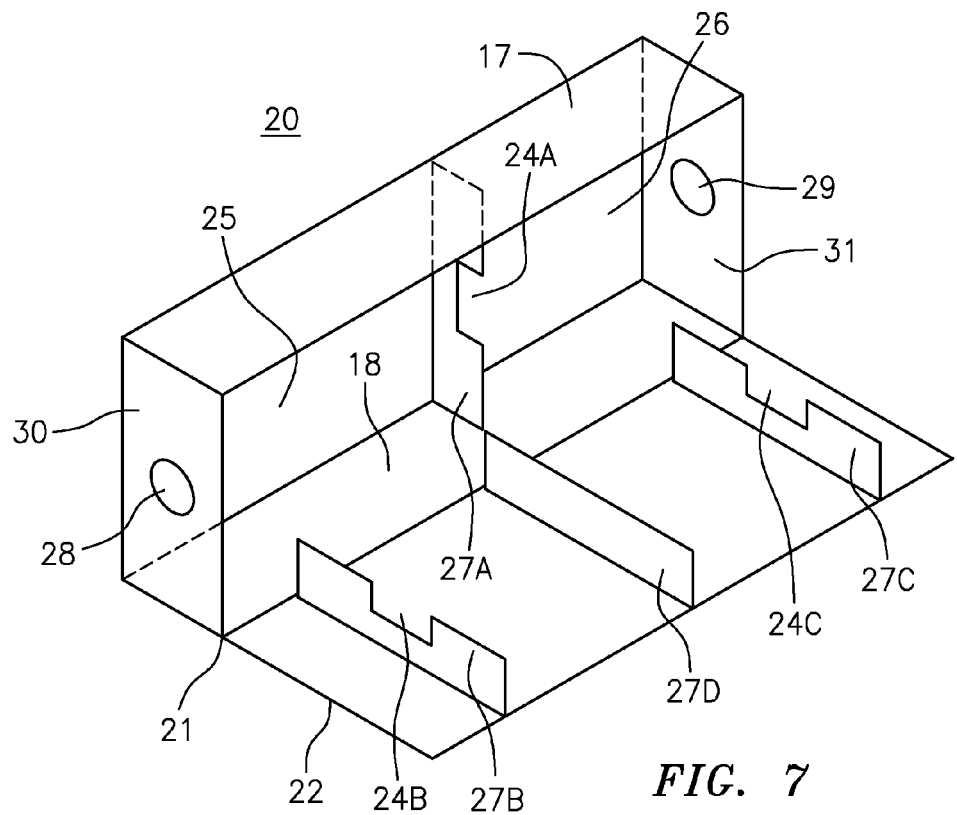
FIG. 7 is a diagram illustrating a plurality of chambers of an encasement, according to an embodiment of the present invention.

Referring now to FIG. 7, FIG. 7 illustrates a plurality of chambers, according to an embodiment of the present invention. Specifically, FIG. 7 illustrates the partitioning of the interior space of the encasement 20 into a plurality of chambers. The encasement 20 also includes a plurality of substrate introduction apertures. Specifically, the encasement 20 includes a first chamber 25 and a second chamber 26 separated by a first chamber wall 27A. The first chamber wall 27A runs between the first sidewall 17 and the second sidewall 18. The first chamber wall 27A includes a bone plate insertion groove 24A upon which the bone plate 100 rests in the encasement 20. The cover 22 includes a second chamber wall 27B and a third chamber wall 27C having a second bone plate insertion groove 24B and a third bone plate insertion groove 24C, respectively, disposed approximately midway between the first chamber wall 27A and the first and second ends 30 and 31. The cover 22 further includes a locking wall 27D that directly opposes the first chamber wall 27A and secures the bone plate 100 in the insertion groove 24A when the cover 22 is closed. The locking wall 27D and the first chamber wall 27A have a height that is less than or equal to a height of the sidewall structure.

The first chamber 25 has a first chamber aperture 28 at the first end 30 and the second chamber 26 includes a second chamber aperture 29 at a second end 31. When the cover 22 is closed, the encasement 20 is sealed except for the first chamber aperture 28 and the second chamber aperture 29 providing an enclosure for coating all surfaces of the bone plate 100.

The embodiment including the first chamber 25 and the second chamber 26 is not limited to two chambers and the encasement 20 may be divided into any number of additional chambers with corresponding openings for injection of the substrate 4. The chamber walls may be configured in any manner within the encasement to properly support the bone plate and allow for proper coating based on a size and shape of the bone plate and the encasement.

By dividing the interior of the encasement 20 into a plurality of chambers, the substrate 4 is injected a reduced distance into the encasement 20 from the plurality of substrate introduction apertures. This reduces the risk that the substrate 4 will begin to dry prior to filling the open interior space of the encasement 20, thus ensuring complete coverage of the bone plate 100 with the substrate 4.

Figure 8:
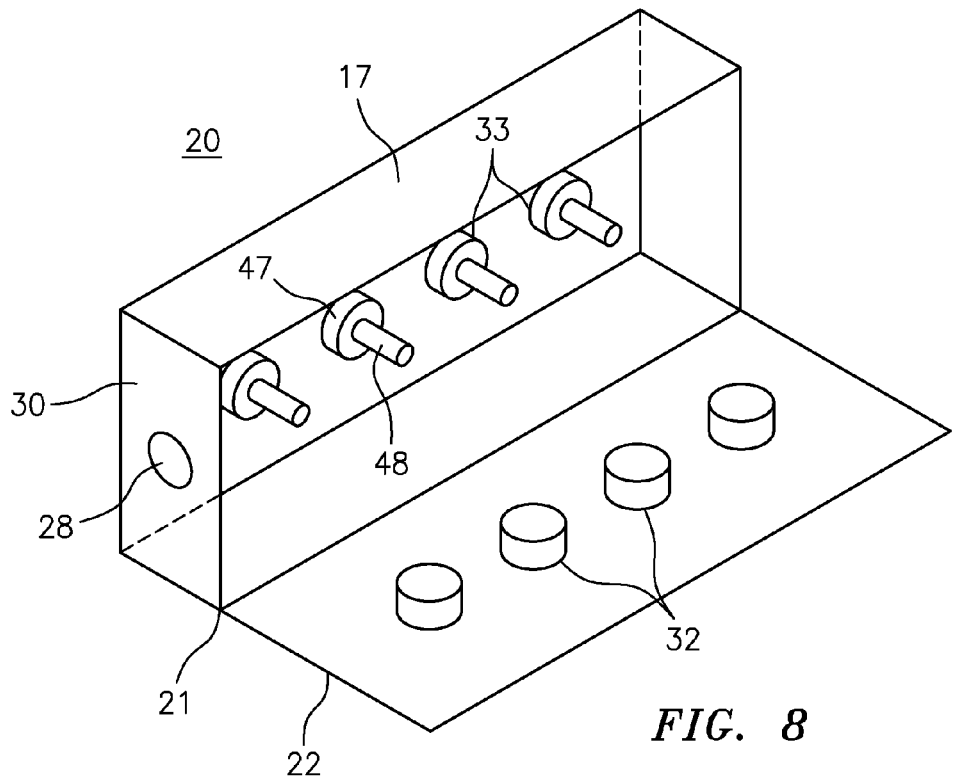
FIG. 8 illustrates a plurality of cover protrusions and a plurality of base protrusions of an encasement, according to an embodiment of the present invention.

Referring now to FIG. 8, FIG. 8 illustrates a plurality of cover protrusions and a plurality of corresponding base protrusions, according to an embodiment of the present invention. Specifically, FIG. 8 illustrates the encasement 20 with a plurality of cover protrusions 32 extending perpendicularly from the cover 22. The cover protrusions 32 fit within and plug the elongated opening 3 of the bone plate 100, and thus prevent access to the screw holes 5 from the top surface 110 of the bone plate 100 when closed within the encasement 20. The cover protrusions 32 occupy the open space of the elongated openings 3, preventing the substrate 4 from entering the elongated openings 3.

The encasement 20 also includes a plurality of base protrusions 33. The base protrusions 33 extend perpendicularly from the base 15 of the encasement 20 to a height less than a height of the sidewall structure. The base protrusions 33 are disposed to extend through and plug the screw holes 5 along the bottom surface 120 of the bone plate 100 when the bone plate 100 is placed within the encasement 20. The base protrusions 33 include a support portion 47 that is wider than the screw holes 5 and upon which the bone plate 100 rests when inserted into the encasement 20. The base protrusions 33 also include a screw portion 48 that is narrower than the support portion 47. The screw portion 48 is disposed on the support portion 47 and extends through the screw holes 5 when the bone plate 100 is inserted into the encasement 20 to align with and rest against the cover protrusions 32.

The base protrusions 33 prevent the substrate 4 from entering the screw holes 5 along the bottom surface 120 of the bone plate 100. The base protrusions 33 meet the cover protrusions 32 within the respective screw holes 5 when the cover 22 is closed. When the bone plate 100 is placed within the encasement 20, there is open space between the top surface 110 and the cover 22 and the bottom surface 120 and the base 15 of the encasement 20. The open space allows for coating of all surfaces of the bone plate 100 when the substrate 4 is injected except for the elongated opening 3 and the bone screw holes 5, as described above. The cover protrusions 32 and the base protrusions 33 are configured according to the placement of the screw holes 5 in the bone plate 100.

Figure 9:
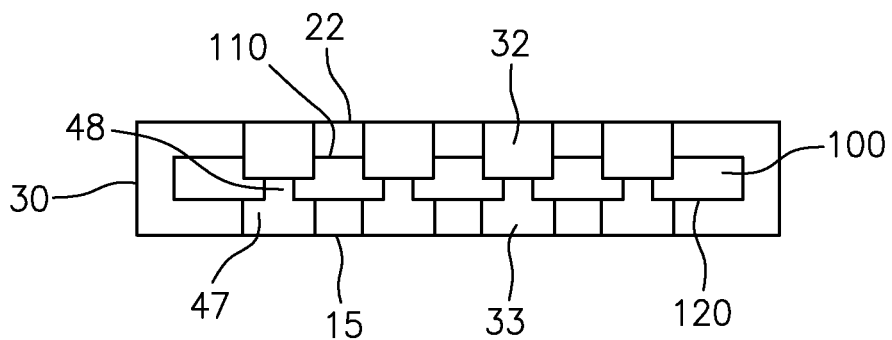
FIG. 9 is a diagram illustrating a cross-sectional view of a bone plate inserted into an open interior space of an encasement, according to an embodiment of the present invention.

Referring now to FIG. 9, FIG. 9 illustrates a cross-sectional view of a bone plate inserted into an open interior space of an encasement, according to an embodiment of the present invention. Specifically, FIG. 9 illustrates the bone plate 100 suspended in an open interior space of the encasement 20. The bone plate 100 is maintained above the base 15 by the support portion 48 and the screw portions 47 extend through the screw holes 5. The cover protrusions 32 and the base protrusions 33 are arranged such that the bone plate 100 does not contact the sidewalls of the encasement 20. Thus, the entire surface of the bone plate 100 can be coated with the substrate 4.

Figure 10A:
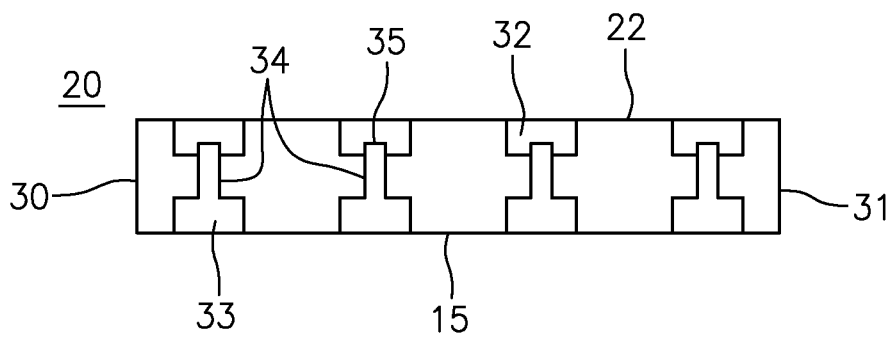
FIG. 10A illustrates a side-view of a further embodiment of an encasement including screw protrusions without a bone plate within the encasement, according to an embodiment of the present invention.

Referring now to FIG. 10A, FIG. 10A illustrates a side-view of another embodiment of an encasement including screw protrusions without a bone plate within the encasement, according to an embodiment of the present invention. Specifically, FIG. 10A illustrates the encasement 20 including screw protrusions 34 extending from the base protrusions 33 into a screw protrusion receiving space 35 of the cover protrusions 32. The screw protrusions 34 and the screw protrusion receiving space 35 assemble in a male to female manner, respectively. When the bone plate 100 is placed within the encasement 20, the screw protrusions 34 extend through the screw holes 5 into the screw protrusion receiving space 35 securing the bone plate 100 in place and maintaining patency of the screw holes 5 while the substrate 4 is injected into the encasement 20.

Figure 10B:
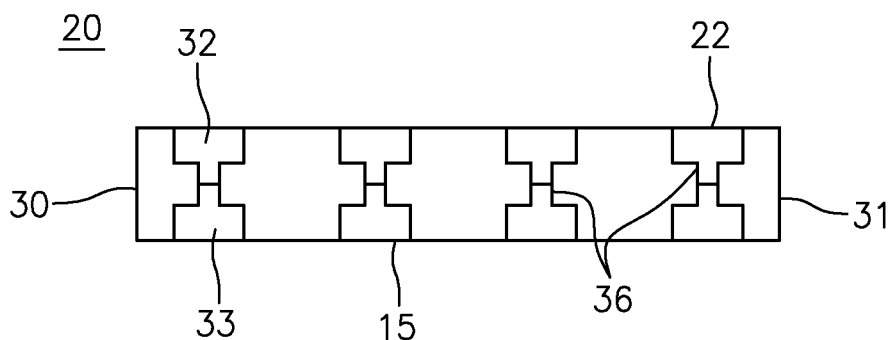
FIG. 10B illustrates a side-view of a further embodiment of an encasement including complementary screw hole protrusions without a bone plate within the encasement, according to an embodiment of the present invention.

Referring now to FIG. 10B, FIG. 10B illustrates a side-view of a further embodiment of an encasement including complementary screw hole protrusions without a bone plate within the encasement, according to an embodiment of the present invention. Specifically, FIG. 10B illustrates complementary screw hole protrusions 36. The screw hole protrusions 36 meet within the screw holes 5 of the bone plate 100 when the bone plate 100 is placed within the encasement 20. The screw hole protrusions 36 secure the bone plate 100 in place and maintain patency of the screw holes 5 while the substrate 4 is injected into the encasement 20.

Cover protrusions 32 may be provided in a serpentine configuration, a configuration aligned parallel to the first end 30, or in an unevenly spaced configuration. Further, the cover protrusions 32 and the base protrusions 33 may be extended from the cover 22 and the base 15, respectively, at varying angles within the encasement 20 to accommodate bone plates that are contoured in a twisted manner to fit a particular bone. The cover protrusions 32 may extend from the cover 22 at an angle complementary to an angle from which the base protrusions 33 extend from the base 15 such that the cover protrusions 32 and the base protrusions 33 meet within the encasement 20.

The encasement 20 is not limited to one shape, but is configured for specific plate types. For example, the size of the encasement 20 for a distal radius plate will mimic that of the distal radius plate by being wider at the first sidewall 17 than at the second sidewall 18.

Similarly, for a distal femoral plate, a proximal tibial plateau plate, a distal fibular plate, and/or a proximal femoral plate, the encasement 20 provides optimal coating by offering a variety of molding constructs for each plate. Further, modular additions accommodate unique aspects of precontoured plates.

Figure 11:
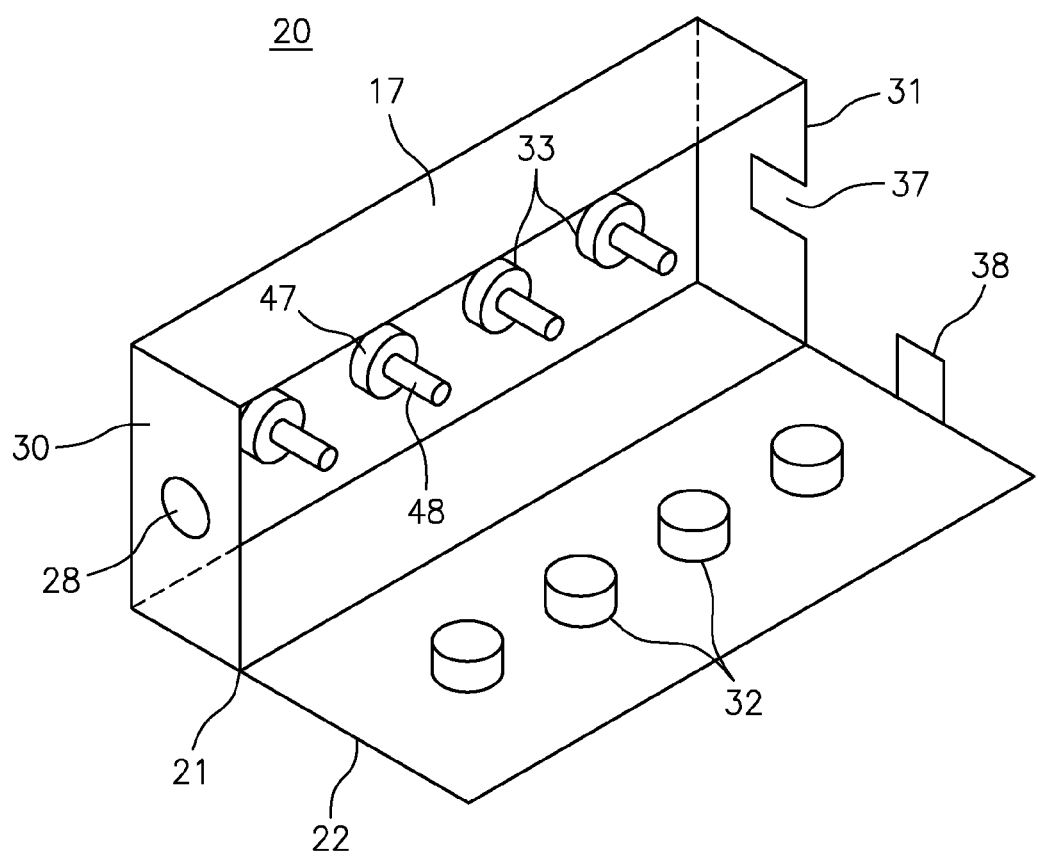
FIG. 11 illustrates a further embodiment of an encasement, according to an embodiment of the present invention.

Referring now to FIG. 11, FIG. 11 illustrates an encasement enabling use of modular additional encasements, according to an embodiment of the present invention. Specifically, FIG. 11 illustrates the encasement 20 designed to accommodate a bone plate having a varying shape, thickness, and length. Specifically, the extension encasement 40 allows the bone plate to be coated with the substrate 4 where a first portion of the bone plate is, for example, rectangular in shape, and a second portion of the bone plate is, for example, circular in shape.

The encasement 20 includes a bone plate exit groove 37 at the second end 31 of the encasement 20 for the bone plate 100 to extend through. The encasement 20 further includes an exit groove lip 38 protruding from the cover 22 to enclose the encasement 20 around the first portion of the bone plate 100 while allowing the second portion of the bone plate 100 to extend through the bone plate exit groove 37. Thus, an additional encasement may be coupled to the encasement 20 to coat the second portion of the bone plate 100 with the substrate 4.

While the invention has been shown and described with reference to certain embodiments of the present invention thereof, it will be understood by those skilled in the art that various changes in from and details may be made therein without departing from the spirit and scope of the present invention as defined by the appended claims and equivalent thereof.

What is claimed is:

1. An encasement for coating a bone plate with a substrate, the encasement comprising:
   a sidewall structure having an upper edge;
   a cover disposed on the upper edge of the sidewall structure and comprising an exterior surface and an interior surface;
   a base from which the sidewall structure rises, wherein the sidewall structure, the cover and the base combine to create an open interior space of the encasement;
   an aperture in the sidewall structure providing access to the open interior space of the encasement;
   a plurality of cover protrusions flush with the exterior surface of the cover and extending from the interior surface of the cover into the open interior space; and
   a plurality of base protrusions extending from the base directly opposing the plurality of cover protrusions,
   wherein a combined height of an individual cover protrusion and an opposing base protrusion is less than or equal to a height of the sidewall structure.

2. The encasement of claim 1, wherein the cover is removably attached to the upper edge of the sidewall structure, wherein the upper edge extends around a periphery of the sidewall structure.

3. The encasement of claim 1, wherein the plurality of cover protrusions fit within openings of the bone plate and the plurality of base protrusions fit within screw holes corresponding to the openings on an opposing side of the bone plate.

4. The encasement of claim 1, wherein the plurality of cover protrusions and the plurality of base protrusions are aligned in one of a serpentine configuration, a linear configuration, and an unevenly spaced configuration.

5. The encasement of claim 1, wherein the plurality of cover protrusions extend perpendicular from the cover and the plurality of base protrusions extend perpendicular from the base.

6. The encasement of claim 1, wherein the plurality of cover protrusions extend at varying angles from the cover and the plurality of base protrusions extend at angles complementary to the varying angles of the cover protrusions from the base.

7. The encasement of claim 1, wherein the bone plate is suspended within the encasement without contacting the interior of the sidewall structure, the cover and the base.

8. The encasement of claim 1, wherein the plurality of base protrusions further comprise a support portion upon which the bone plate rests and a screw portion extending from the support portion, wherein the screw portion is narrower in width than the support portion.

9. The encasement of claim 3, wherein the plurality of cover protrusions and the plurality of base protrusions prevent the substrate from entering the openings and the screw holes of the bone plate, respectively.

10. The encasement of claim 1, wherein the sidewall structure comprises a groove that allows the bone plate to extend out from the encasement, and wherein a groove lip extends from the cover to enclose the encasement around a first portion of the bone plate when the cover is closed.

11. The encasement of claim 1, wherein the cover protrusions are coupled to the interior surface of the cover and extend from the cover beginning at a position adjacent to the upper edge of the sidewall structure.

12. The encasement of claim 1, wherein the aperture is flush with the exterior surface of the sidewall structure.

\* \* \* \* \*